United States Patent [19]

Libman et al.

[11] 4,040,909
[45] Aug. 9, 1977

[54] DIAGNOSTIC DEVICE FOR A LIQUID SAMPLE

[75] Inventors: Gary Libman, Des Plaines; Frank K. Villari, Oak Park, both of Ill.

[73] Assignee: The Kendall Company, Boston, Mass.

[21] Appl. No.: 634,110

[22] Filed: Nov. 21, 1975

Related U.S. Application Data

[62] Division of Ser. No. 495,978, Aug. 29, 1974, Pat. No. 3,952,729.

[51] Int. Cl.² .............................................. C12K 1/10
[52] U.S. Cl. .............................. 195/127; 195/103.5 M
[58] Field of Search .............................. 195/139, 127

[56] References Cited

U.S. PATENT DOCUMENTS

| | | | |
|---|---|---|---|
| 2,992,974 | 7/1961 | Belcove et al. | 195/139 |
| 3,563,859 | 2/1971 | Fink | 195/127 |
| 3,589,983 | 6/1971 | Holderith et al. | 195/139 |
| 3,632,478 | 1/1972 | Fink | 195/139 |
| 3,728,228 | 4/1973 | Duranty | 195/127 |
| 3,830,701 | 8/1974 | Stussman et al. | 195/139 |
| 3,838,013 | 9/1974 | Bergeron | 195/139 |
| 3,849,256 | 11/1974 | Linder | 195/139 |
| 3,890,203 | 6/1975 | Mehl | 195/139 |
| 3,919,053 | 11/1975 | Nazemi | 195/139 |

Primary Examiner—Alvin E. Tanenholtz
Attorney, Agent, or Firm—Powell L. Sprunger

[57] ABSTRACT

A diagnostic device for a liquid sample comprising, a receptacle having a cavity containing a culture medium, and means for establishing communication with the sample. The device has pump means for withdrawing and expelling liquid, and valve means for separately establishing communication of the establishing means and the receptacle with the pump means, in order that a liquid sample may be withdrawn by the pump means through the establishing and valve means and expelled by the pump means through the valve means into the receptacle for inoculation of the culture medium.

2 Claims, 12 Drawing Figures

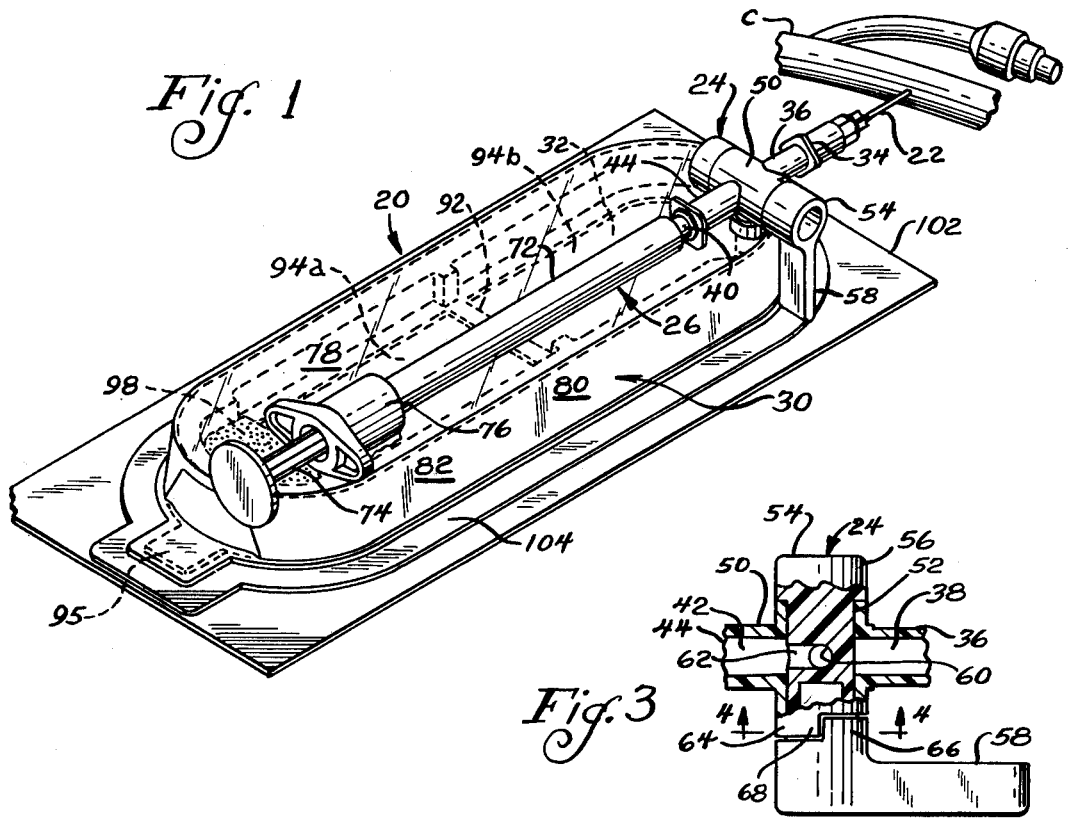
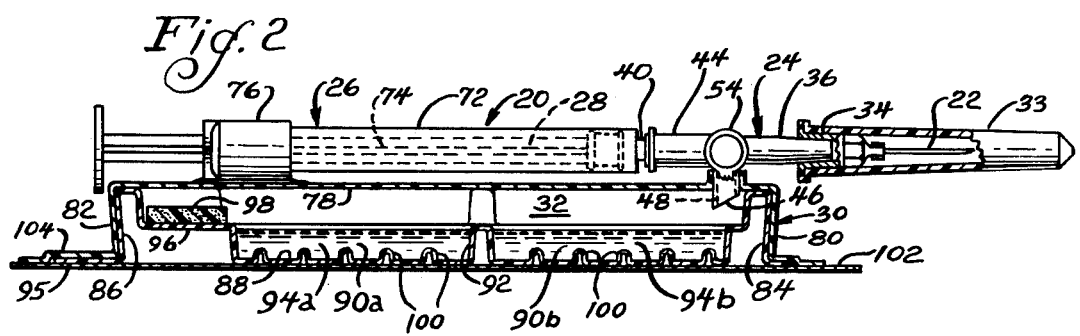
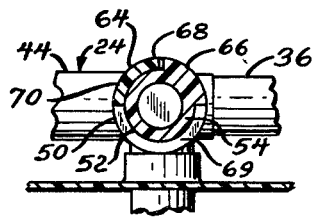

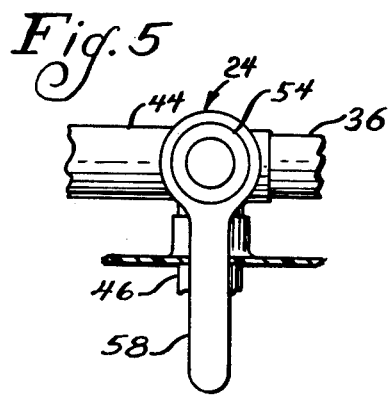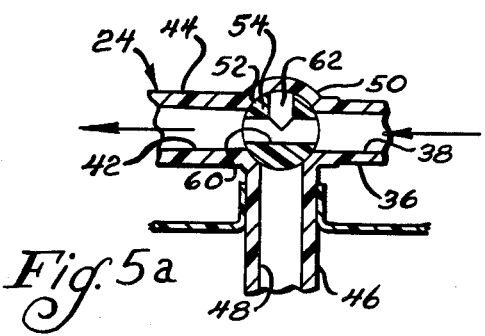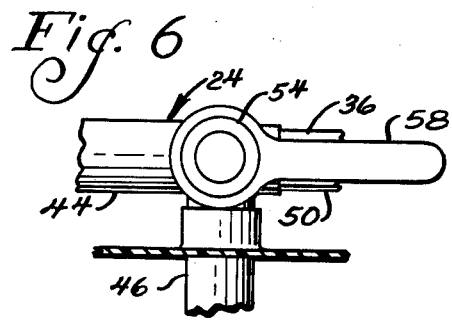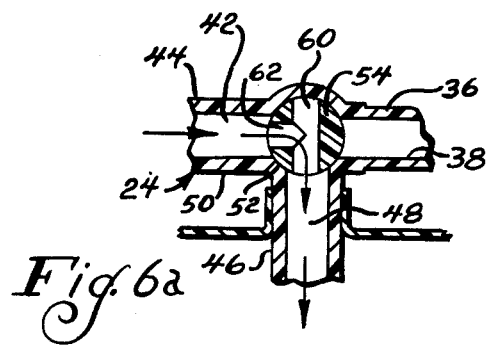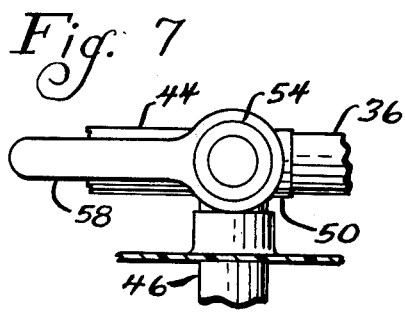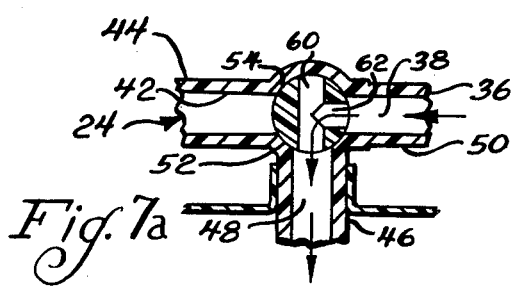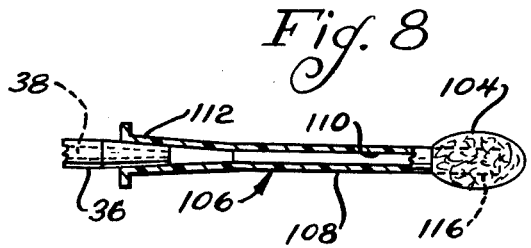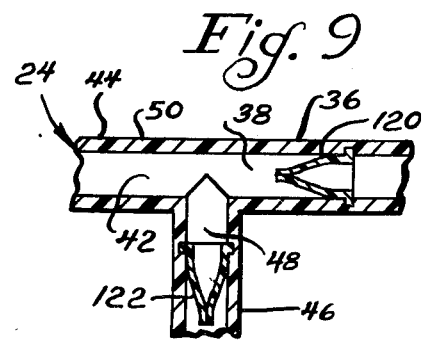

DIAGNOSTIC DEVICE FOR A LIQUID SAMPLE

This is a division of application Ser. No. 495,978, filed Aug. 29, 1974, now U.S. Pat. No. 3,952,729.

BACKGROUND OF THE INVENTION

The present invention relates to diagnostic devices, and more particularly to a device for diagnosing a liquid sample.

It is frequently desirable to determine the presence of bacteria in body fluids of a patient, such as blood or urine, for purposes of diagnosis. For example, a major problem confronting hospitals today is the determination of urinary tract infections. Although chills, fever, dysuria and frequency of urination may indicate infection, the incidence of asymptomatic urinary tract infection has been shown to be a common occurence. This asymptomatic infection is clinically diagnosed by testing for bacteriuria, which literally means the presence of bacteria in the urine. Clean voided urine from normal individuals generally contains microorganisms, which are indigenous residents of the urethra. Urine in the bladder, on the other hand, is ordinarily sterile, and the presence of any bacteria in the upper urinary tract is considered abnormal. Significant bacteriuria is a term that has been used to describe the numbers of bacteria in voided urine that exceed the numbers usually due to contamination from the anterior urethra and are in the range of the bacterial titers usually found in infected bladder urine. It has been established that a guideline for determination of bladder bacteriuria is the presence of 100,000 or more bacteria per milliliter in whole voided urine, although 70 to 85% of most cases of bacteriuria are characterized by counts of over 1,000,000 organisms per milliliter.

Since the presence of bacteriuria may be determined by the number of organisms in the urine, it has been found advantageous to use culture media for determining the number of bacteria in a sample of the urine. Presently hospitals and laboratories frequently collect a sample of body fluid, such as urine or blood, in a receptacle, and transfer the collected fluid from the receptacle to a culture bottle. However, the time lag encountered with this type of procedure presents a recurrent problem, and may cause unreliability in the test results. For example, urine presents an ideal growth medium for microorganisms, and certain species of bacteria may double in number in as little as 20 minutes. Accordingly, the assessment of urine for bacteriuria should be made immediately after the specimen is voided, since a sufficient time lag makes a distinction between significant infection and an overgrowth of contaminants impossible. Likewise, other microorganisms are so sensitive to their environment that they are unable to survive the delay, and the inoculation media will not present a true picture for the diagnostician. Thus, it is desirable to reduce the delay between taking the sample of the body fluid and the subsequent inoculation of culture medium with the sample, as well as preventing contamination of the sample.

SUMMARY OF THE INVENTION

A principle feature of the present invention is the provision of a device of simplified construction for diagnosing the presence of bacteria in a liquid sample.

The diagnostic device of the present invention comprises a receptacle having a cavity containing a culture medium, and means for establishing communication with the sample. The device has pump means for withdrawing and expelling liquid, and valve means for separately establishing communication of the establishing means and the receptacle with the pump means.

Thus, a feature of the invention is that the liquid sample may be withdrawn by the pump means through the establishing and valve means preparatory to inoculation of the culture medium.

Another feature of the invention is that the withdrawn sample may be expelled by the pump means through the valve means into the receptacle for inoculation of the culture medium.

A further feature of this invention is that the device permits inoculation of the medium with the sample in a simplified manner.

A feature of the invention is that the device permits a closed-system transfer of virtually any body fluid, human or animal, into the culture medium.

Thus, another feature of the invention is that the culture medium is inoculated with the liquid sample without contamination of the sample.

Yet another feature of the invention is that the culture medium is inoculated substantially immediately after withdrawing the sample.

A feature of the invention is that in one embodiment the establishing means comprises a hollow needle for penetrating a source of liquid sample, such as urine in a catheter.

A further feature of the invention is that the establishing means comprises an elongated hollow member communicating with the valve means and having a swab adjacent an end distal the valve means, in order to introduce and spread a sterile suspension liquid for the sample at the sample site.

Still another feature is the provision of a method of preparing a sample for diagnosis.

Further features will become more fully apparent in the following description of the embodiments of this invention and from the appended claims.

DESCRIPTION OF THE DRAWINGS

In the drawings:

FIG. 1 is a perspective view of a diagnostic device of the present invention as positioned for taking a liquid sample from a catheter;

FIG. 2 is an elevational view, taken partly in section, of the diagnostic device of FIG. 1;

FIG. 3 is a fragmentary top view of a valve assembly, taken partly in section, in the diagnostic device of FIG. 1, with a handle in the assembly rotated 90 degrees;

FIG. 4 is a fragmentary sectional view taken substantially as indicated along the line 4—4 of FIG. 3;

FIGS. 5 and 5a are fragmentary elevational and sectional views, respectively, showing a valve element in the valve assembly of FIG. 3 located at a first position;

FIGS. 6 and 6a are fragmentary elevational and sectional views, respectively, showing the valve element in the valve assembly of FIG. 3 located at a second position;

FIGS. 7 and 7a are fragmentary elevational and sectional views, respectively, showing the valve element in the valve assembly of FIG. 3 located at a third position;

FIG. 8 is a fragmentary sectional view of a swab attachment for the diagnostic device of FIG. 1; and FIG. 9 is a fragmentary sectional view of another embodiment of a valve assembly for the diagnostic device of FIG. 1

DESCRIPTION OF THE PREFERRED EMBODIMENTS

Referring now to FIGS. 1 and 2, there is shown a diagnostic device generally designated 20 having a hollow needle 22 for penetrating a source of a liquid sample, such as a source of urine through the wall of a catheter C, a valve assembly 24 communicating with the needle 22, a syringe or pump means 26 having a chamber 28 communicating with the valve assembly 24, and an elongated receptacle 30 having a cavity 32. The needle 22 has a hub 34 removably received on a stem 36 extending forwardly from the valve assembly 24, such that the needle communicates with a first passageway 38 in the stem 36, as best illustrated in FIGS. 1-3. As shown in FIG. 2, an elongated cap 33 may be removably positioned on the needle 22 for covering and protecting the needle when the device is not in use. As best illustrated in FIGS. 1-3, the syringe 26 has a nipple 40 received in a second passageway 42 in a second stem 44 extending rearwardly from the valve assembly 24. The first and second passageways 38 and 42 are preferably aligned for a purpose which will be described below. The valve assembly 24 has a third stem 46 having a third passageway 48 extending generally at right angles to the first and second passageways 38 and 42. Thus, the valve assembly 42 communicates through the first passageway with the hollow needle 22, the second passageway 42 with the syringe chamber 28, and the third passageway 48 with the container cavity 32.

As illustrated in FIGS. 3 and 5a, the valve assembly 24 has a body member 50 having a cylindrical bore 52 extending through the body member. The valve assembly also has a cylindrical valve member 54 rotatably received in the bore 52, with the valve member 54 having a plug 56 adjacent one end to retain the valve member in the bore, and a handle 58 adjacent the other end for rotating the valve member in the bore. The valve member 54 has a first channel 60 which extends through the valve member and which is aligned with the first and second passageways 38 and 42 when the handle and valve member are located at a first position, as shown in FIGS. 5 and 5a. In this configuration of the valve assembly 24, the handle 58 of the valve member 54 is directed along the third stem 46, as shown in FIG. 5, and fluid communication is established between the needle and the syringe chamber through the first channel 60.

The handle 58 of the valve member 54 may be moved to a second position directed along the first stem 36, as shown in FIG. 6. In this configuration of the valve assembly, a second channel 62, which extends between the first channel 60 intermediate its ends and the outside of the valve member 54, communicates between the second passageway 42 and the first channel 60, as shown in FIG. 6a, and the first channel 60 communicates with the third passageway 48. Thus, in this configuration of the valve assembly, communication is established between the syringe chamber and the container cavity.

The handle 58 of the valve member 54 may be moved to a third position directed along the third stem 44 of the valve assembly, as illustrated in FIG. 7. In this configuration of the valve assembly, communication is established between the needle and receptacle cavity through the first passageway 38, the second channel 62, the first channel 60, and the third passageway 48, as shown in FIG. 7a. Accordingly, communication between the needle and the syringe chamber, the syringe chamber and the container cavity, and the needle and the container cavity may be selected by movement of the handle 58 of the valve member 54.

As shown in FIGS. 3 and 4, the body member 50 of the valve assembly has a projection 64 extending toward the handle 58. A lug 66, which extends outwardly from the valve member 54, is located in a cutout portion 69 intermediate first and second ends 68 and 70, respectively, of the projection 64. The projection 64 and lug 66 cooperate in serving as stop means to limit movement of the valve member 54 in the body member 50. When the lug 66 engages against the first end 68 of the projection 64, the valve element is located at its second position, as shown in FIGS. 6 and 6a, with its handle 58 directed along the first stem 36, and with the valve assembly communicating between the syringe chamber and the container cavity. When the lug 66 is engaged against the second end 70 of the projection 64, the handle 58 is directed along the second stem 44 of the valve assembly, with the valve assembly communicating between the needle and the container cavity in its third position, as shown in FIGS. 7 and 7a. When the lug 66 is positioned midway between the first and second ends 68 and 70 of the projection 64, the handle 58 is directed along the third stem 46 of the valve assembly in its first position, as shown in FIG. 5, and the valve assembly communicates between the needle and the syringe chamber as best illustrated in FIG. 5a. Thus, the lug 66 and projection 64 serve to limit movement of the valve member 54 in the body member 50 between the second and third positions of the valve assembly.

As illustrated in FIGS. 1 and 2, the syringe 26 has a barrel 72 defining the syringe chamber 28, and a plunger 74 received in the syringe chamber 28 for reciprocation therein and pumping of liquid into and out of the chamber. A band 76 extends from a top wall 78 of the receptacle 30 around the syringe barrel 72 to retain the syringe in position on top of the receptacle.

The receptacle 30 has a first outer portion 80 defined by the top wall 78 and a depending side wall 82 extending peripherally around the top wall 78. A second inner portion 84 of the receptacle is removably received in the outer portion 80, with a peripheral flange 86 of the inner portion engaging against the side wall 82 of the outer portion 80 to retain the inner portion in the outer portion of the receptacle. The inner portion 84 has a bottom wall 88 having a pair of compartments 90a and 90b separated by a partition 92. Different types of culture medium 94a and 94b are located in the compartments 90a and b, respectively, as shown. The bottom wall 88 of the inner portion 84 has a step 96 adjacent an end of the inner portion 84 remote the third stem 46 of the valve assembly 24. An absorbent pad 98, such as a compressed cellulose material or a sponge, is positioned on the step 96 for a purpose which will be described below. The bottom wall 88 of the compartments 90a and b has a plurality of protuberances 100 to retain the culture media 94a and b in position in the compartments.

In preparation of the device for taking a sample, the inner portion 84 of the receptacle 30 may be removed from the outer portion 80 through use of a tab 95 extending from one end of the inner portion 84, and appropriate media may be placed in the compartments. The inner portion 84 of the receptacle may then be inserted into the outer portion until the flange 86 engages the side wall 82 of the outer portion 80. A fluid impervious sheet 102, such as foil, may then be secured to an outwardly directed flange 104 extending peripherally around the side wall 82 of the outer portion 80, such that the sheet 102 seals the inner portion 84 inside the outer portion 80 of the receptacle, and prevents moisture loss from the receptacle cavity 32 and thus possible breaking up of the media in the receptacle cavity.

The device may be used to collect a liquid sample as follows. The handle 58 of the valve member 54 is moved to its first position, as shown in FIGS. 5 and 5a, such that the handle 58 is directed along the third stem 46, and the cap 33 is removed from the needle. The needle 22 may then be used to penetrate the source of liquid sample. If the device is utilized to obtain a urine sample from a catheter C, as shown in FIG. 1, by penetrating the wall of the catheter with the needle, the catheter is first blocked below the site of the needle puncture to collect a sufficient amount of urine in the catheter where the sample is to be taken.

Once the needle has penetrated the catheter wall, the plunger 74 of the syringe is withdrawn from the syringe barrel 72 to withdraw urine from the catheter through the needle 22, the first passageway 38, the first channel 60, and the second passageway 42 into the syringe chamber 28. When a sufficient sample has been withdrawn from the catheter, the handle 58 of the valve element 54 is moved to the second position directed along the first stem 36, as shown in FIGS. 6 and 6a, and the needle 22 may be withdrawn from the catheter, if desired. Next, the barrel 74 of the syringe 26 is pushed into the chamber 28 to pump the withdrawn liquid sample through the second passageway 42, the second channel 62, the first channel 60, the third passageway 48 into the receptacle cavity 32. As the liquid sample passes from the third passageway 48 into the receptacle cavity 32, the third stem 46 directs the liquid to one end of the culture media, after which it flows along the surface of the longitudinally aligned media 94b and 94a for inoculation thereof, with any excess liquid continuing to flow into the absorbent pad 98 where it is absorbed and retained. Thus, any excess liquid is drawn off the surface of the culture media 94a and 94b, after the media 94a and b has been inoculated. If it is desired to obtain a greater quantity of liquid sample for inoculation of the media, the needle may be retained in place through the wall of the catheter, while the valve element is repetitively moved between its first and second positions, and the syringe is repetitively pumped to withdraw liquid from the catheter and pump it into the receptacle cavity. In either event, once the culture media has been inoculated by the liquid sample, the needle 22 may be removed from the first stem 36, and the receptacle presents a convenient package for subsequent incubation of the media. After suitable incubation, the color attained by the media and the density of the bacterial colonies provide an indication of the amount of bacteria which was initially present in the liquid sample for diagnosing the sample.

It is thus apparent that the device of the present invention permits immediate inoculation of the culture media with the liquid sample in a simplified manner. The needle permits penetration of the liquid source and the device provides a closed system for inoculating the media with the sample, thus preventing contamination of the sample. It is apparent that the device of the present invention may be used for taking samples of body fluids other than urine, such as blood, or spinal fluid, for inoculation of suitable media. It is also contemplated that the device may be used for diagnosing the body fluids of animals. The particular media 94a and b which is used in the receptacle is selected according to the fluid to be diagnosed and bacteria to be detected. Suitable media for use in determining the bacteria count in urine samples is CLED and MacConkey. Similarly, suitable media for determining the bacteria count in a sample of spinal fluid are blood agar and chocolate agar. Media useful for determining the bacteria count in blood are blood agar and chocolate agar. It is also apparent that a single medium or more than two media may be used in the receptacle, if desired. If a liquid sample is to be taken where the use of a syringe may be undesired, such as the spinal column, or the liquid sample is in an environment of sufficiently high pressure, the handle 58 may be moved to the third position directed along the second stem 44 of the valve assembly, as shown in FIGS. 7 and 7a, such that communication is established between the needle and the receptacle cavity. Thus, in this configuration of the valve member, fluid passes directly from the needle through the valve assembly to the receptacle cavity for inoculation of the media.

For certain applications it is desirable to use the swab attachment 106, as shown in FIG. 9 in lieu of the needle. The attachment 106 has an elongated hollow member 108 having a passageway 110 extending longitudinally through the member 108. One end 112 of the hollow member 108 is slightly flared and may be removably attached to the outer end of the first stem 36 of the valve assembly 24, such that the passageway 110 of the hollow member 108 is in communication with the first passageway 38 of the valve assembly 24. The hollow member 108 has a swab 104, such as cotton, adjacent the other end 116 of the hollow member 108. The hollow member 108 may be used in conjunction with the device of the present invention for obtaining a sample from the site of a wound as follows. First, a liquid suspension solution, such as a saline solution, e.g., isotonic sodium chloride, is withdrawn into the syringe of the device, and ejected by the syringe to the swab and wound site, since there may not be a sufficient quantity of liquid initially present at the site to obtain an adequate sample with the device. Once the solution has been ejected against the wound site, and the solution is mixed by the swab with the sample to obtain suspension of the sample in liquid solution. Next, the solution, which contains the suspended sample, is withdrawn into the syringe and pumped into the receptacle cavity, as previously described, to inoculate the culture media.

Another embodiment of a valve assembly for the device of the present invention in FIG. 10, in which like reference numerals designate like parts. In this embodiment of the valve assembly, a first one-way valve element 120, such as a flap valve, is positioned in the first passageway 38 of the first stem 36, such that the valve element permits liquid to pass through the first passageway to the second passageway 42, but prevents passage of liquid from the second and third passageway 42 and 48 through the first passageway 38. A second valve element 122 is located in the third passageway 48 of the third stem 46, such that liquid is permitted to pass from the second passageway 42 through the third passageway 48, while liquid is prevented from passing through the third passageway 48 to the first or second passageways 38 or 42. In use, when the needle or swab attachment has been located at the desired position for obtaining a liquid sample, the plunger of the syringe is withdrawn from the syringe barrel to withdraw liquid through the needle or swab attachment, the first valve element 120 in the first passageway 38, and the second passageway 42 into the syringe chamber. At the same time, the second valve element 122 prevents passage of liquid from the receptacle cavity to the syringe chamber. Next, the syringe plunger is pushed into the syringe barrel, and the withdrawn sample is pumped through the second passageway 42 and the second valve element 122 into the receptacle cavity for inoculation of the culture media, while the first valve element 120 prevents passage of the pumped liquid through the first passageway 38 into the needle or swab attachment.

Thus, there has been described a diagnostic device for inoculating culture media with a liquid sample in a simplified and aseptic manner, substantially immediately after the sample has been taken. During use, the needle or swab attachment serve to establish communication with the liquid sample, and the valve assembly or valve means separately establishes communication of the needle or swab attachement and the receptacle with the syringe.

The foregoing detailed description is given for clearness of understanding only, and no unnecessary limitations should be understood therefrom, as modifications will be obvious to those skilled in the art.

What is claimed is:

1. A diagnostic device for a source of liquid sample, comprising:
    an elongated receptacle having a culture medium longitudinally disposed in a generally planar configuration along a wall of the receptacle;
    pump means connected intermediate the source and receptacle;
    means in addition to the pump means for directing the sample from the pump means into the receptacle only adjacent one end of said medium for passage along the medium; and
    an absorbent pad located adjacent the other end of the medium remote from the directing means to capture and retain excess liquid.

2. The device of claim 1 wherein said receptacle includes a plurality of longitudinally aligned culture media, and the directing means directs the sample adjacent one end of the aligned media.

* * * * *